United States Patent [19]

Esposito

[11] 4,144,046

[45] Mar. 13, 1979

[54] METHOD OF STIMULATING THE FLOW OF LATEX AND COMPOSITIONS USED THEREIN

[75] Inventor: James E. Esposito, Ft. Washington, Pa.

[73] Assignee: Amchem Products, Inc., Ambler, Pa.

[21] Appl. No.: 585,208

[22] Filed: Jun. 9, 1975

Related U.S. Application Data

[63] Continuation of Ser. No. 86,342, Nov. 2, 1970, abandoned.

[51] Int. Cl.$^2$ .............................................. A01N 9/36
[52] U.S. Cl. ..................................... 71/86; 71/DIG. 1
[58] Field of Search ............................. 71/86, DIG. 1

[56] References Cited

U.S. PATENT DOCUMENTS

| 3,172,816 | 3/1965 | Swintosky | 71/DIG. 1 |
| 3,343,941 | 9/1967 | Baltazzi | 71/DIG. 1 |
| 3,484,229 | 12/1969 | Floyd | 71/DIG. 1 |
| 3,736,112 | 5/1973 | Abramitis | 71/DIG. 1 |
| 3,756,801 | 9/1973 | Herschler | 71/65 |
| 3,776,857 | 12/1973 | Lindner | 71/DIG. 1 |

FOREIGN PATENT DOCUMENTS

| 953533 | 3/1964 | United Kingdom | 71/DIG. 1 |
| 1160674 | 8/1969 | United Kingdom | 71/DIG. 1 |

OTHER PUBLICATIONS d'Auzac et al., "Physiologie Vegetable L'ethylene, etc;" (1969) Comp. Rend. Acad. Sc. t. 268 pp. 3046-3049 (1969).

Matsumoto et al., "Oxid. of Methyl Linoleate etc;" (1970) CA 74 No. 49828t. (1971).

*Primary Examiner*—Glennon H. Hollrah

[57] ABSTRACT

A latex stimulant and method of use involving a composition comprised of (a) ethephon (2-chloroethylphosphonic acid) and its functional derivatives, (b) and a thickening agent so that the composition may be used to stimulate the flow of latex in rubber trees through direct application by brush to the bark of the tree or to exposed areas wherein the bark has been removed.

14 Claims, No Drawings

METHOD OF STIMULATING THE FLOW OF LATEX AND COMPOSITIONS USED THEREIN

This is a continuation of application Ser. No. 86,342, filed Nov. 2, 1970 now abandoned.

This invention relates to a latex stimulant and method of use in connection with rubber plants.

It is well known to extract latex from growing rubber plants by the selective removal of bark of the plant which allows the latex to drain into a strategically placed vessel. Heretofore certain agents have been employed to stimulate or increase the flow of latex, the most widely used of which is 2,4,5-trichlorophenoxyacetic acid in small amounts.

The use of ethephon, i.e., 2-chloroethylphosphonic acid, as a growth regulating agent, is still in its infancy, but it is clear that ethephon is having a revolutionary effect in agricultural circles. Reference is made to presently pending U.S. application Ser. No. 869,386 which discloses and claims the use of ethephon and its functional derivatives in growth regulating processes.

It has been discovered that the use of water thin ethephon composition was not completely satisfactory for application to the bared trunks of rubber plants since much of the aqueous ethephon solution would immediately run off when applied to the bared surface, and furthermore, in the tropics, such as Malaysia, the extensive rains would wash the remaining ethephon composition away.

While attempts were made to increase the viscosity of the ethephon composition, nevertheless, the extremely high acidity (pH 1 to 1.5) of an aqueous composition involving ethephon had a deleterious effect upon the conventional thickening agents.

In view of all of the foregoing it is an object of the present invention to provide a latex stimulant and method of use wherein a stable composition is presented that has fairly extensive shelf life.

Another object of the present invention is to provide a latex stimulant and method of use involving ethephon wherein the latex stimulant composition can be provided in a single container that can be shipped thousands of miles to the point of use.

Still another object of the present invention is to provide a latex stimulant and method of use which will readily blend with a vegetable oil or fat, such as palm oil, palm kernel oil, cocoanut oil or corn oil in substantial amounts.

Still another object of the present invention is to provide a latex stimulant and method of use including a composition that can be modified to include an anti-oxidant, a bactericide or preservative, as well as an additional solvent in order to make a compatible mixture.

The foregoing as well as other objects of the invention are achieved by providing a composition which is basically comprised of ethephon and a thickening agent.

Ethephon is the common name for 2-chloroethylphosphonic acid that has been approved by the American National Standards Institute. The method of preparation of this compound and its functional derivatives as well as the various methods of use are set forth in presently pending U.S. application Ser. No. 869,386 which is expressly incorporated herein by reference. The ethephon may be formulated with the other components of the invention either by using essentially pure ethephon or even ethephon of a technical grade of 90% (plus or minus 2%) solution by weight. The ethephon is blended with a thickening agent as set forth in the next paragraph.

Typical examples of thickening agents which can be employed in the practice of the present invention are polysaccharide gums such as gum tragacanth, locust bean gum, gum acacia, and polysaccharides produced by the fermentation of a carbohydrate by the bacterium, Xanthomonas campestris. Natural resins, such as gum Damar, have also been effective in the practice of the present invention. Preferably, a polysaccharide gum, such as Biopolymer XB-23 should be employed. The Biopolymer XB-23 is an anionic heteropolysaccharide produced by the fermentation of a carbohydrate by the bacterium Xanthomonas campestris. The Biopolymer XB-23 molecule is made up of repeating groups each of which consist of a block of 16 hexose residues with an order of arrangement and linkage of glucoronic acid, mannose, and glucose. This thickener is made by Central Research Laboratories Division of the General Mills Company of Minneapolis, Minnesota. This thickener has an unusual resistance to degradation by acids and has been found to perform quite satisfactorily at a pH of 1 to 1.5. The mixture produced by combining XB-23 and the ethephon solution is pseudoplastic. The other thickening agents set forth hereinbefore also produce stable and effective acid compositions at a pH of 1 to 1.5.

It will be appreciated that the composition of the present invention will have a gelatinous consistency. In the preferred embodiment of the present invention the composition should have a viscosity of from about 1,000 centipoises to about 10,000 centipoises when measured by a Brookfield Viscometer Model RVT, employing a number 4 spindle at 20 rpm, wherein the composition temperature is 25° C.

In order to formulate the composition of the present invention, it has been found that significant amounts of water will be used. In many instances it will be desirable to add a vegetable oil or fat, such as palm oil, palm kernel oil, cocoanut oil or corn oil in amounts of between 5 to 50% by weight. Ethephon should be present in a range of from about 1% to about 20% by weight, and the thickening agent should comprise from about 0.5% to about 10% by weight of the latex stimulant composition.

One aspect of the present invention provides a composition which possesses the necessary heavy consistency without the addition of a thickening agent. By employing an emulsifying agent in a composition consisting of ethephon and the vegetable fat or oil, a stable invert emulsion, i.e., a water-in-oil emulsion, wherein the ethephon is in the water phase, can be formed. The invert emulsion can be satisfactorily employed as herein provided to promote increased latex flow. The emulsifying agent should comprise from about 3% to 12% by weight of said invert emulsion.

The emulsifier utilized herein can be any suitable agent known to the art which will form a water-in-oil emulsion. Particularly satisfactory results can be obtained employing an emulsifying agent selected from the group of oxyalkylene derivatives of long-chain aliphatic amides and amines, polyoxyethylene sorbitol poly-fatty acid esters, and fatty acid esters of hexitan.

The composition or formulation may also contain an anti-oxidant, a bactericide, a water repellent, a bark penetrant, and such solvents as are necessary to produce a compatible mixture.

The anti-oxidant is used to prevent or lessen rancidity and polymerization of the vegetable oil or fat. In some cases the vegetable oil or fat assists in lending water repellant properties to the latex stimulant composition, and in such cases the anti-oxidant is preferably used.

The bactericide or preservative is of a nature that will readily occur to those skilled in the art, and serves to prevent or lessen biodegredation of the thickening agent.

In some cases the oil or fat in the composition will attract insects. An insect repellant can be included in the formulation where necessary.

In preparing formulations in accordance with the present invention it has been found useful to rely upon certain solvents in order to hasten the formulation as well as to enhance the stability and shelf life of the finished product. Formulation takes place at room temperature.

The compositions of the present invention are used in accordance with well known practices in the art. Strips of bark of the rubber plant are removed, creating what are referred to in the art as tapping cuts, and the composition is simply applied by brush directly to the bark at a point immediately below the stripped area or in some cases the composition may be applied to the exposed area. In another method of application, the bark is lightly scraped below the tapping cut and the composition is applied onto the lightly scraped area.

While there is no intention to limit the operation of the present invention to any particular theory, nevertheless, ethephon is believed to be effective because it has the ability to break down into or otherwise liberate ethylene within the plant tissues. In the practice of the present invention the liberation of ethylene is believed to initiate a biological activity that takes the form of unplugging the severed ends of the latex vessels, thereby prolonging the flow of latex.

In some cases the penetration of compositions of the present inventions into the rubber plant is enhanced by the addition of a bark penetrant to the formulation. Typical examples of bark penetrants which can be employed herein are dibutylphthalate, diisooctylphthalate, dioctylphalate and dimethylphthalate. In any case, the composition may be simply applied to the trunk of the rubber tree through the use of a brush or other coating or spray equipment that will readily occur to those skilled in the art.

Reference is now made to the following examples which set forth formulations embodying the latex stimulant and method of use of the present invention, it being understood that such examples are presented for the purposes of illustration only and are not necessarily limiting upon the scope of the invention.

EXAMPLE A

A typical latex stimulant comprising the present invention contained the following:

| | | |
|---|---|---|
| Ethephon | (39.5 wt. per cent ethephon) (30 wt. per cent propylene glycol) (30.5 wt. per cent water) | 2.689 |
| Thickener | (Biopolymer XB-23) | 0.089 |
| Solvent | (Butyrolactone) | 0.177 |
| Water | | 5.910 |
| | | 8.865 lbs. |

The foregoing composition had a specific gravity of 1.065 at 20° C. It was formulated by preparing a slurry of the thickener and a solvent. The slurry was added rapidly to the mixture of ethephon and water under agitation at ambient conditions.

EXAMPLE B

A formulation including palm oil was prepared as follows:

| | |
|---|---|
| Ethephon (4 molar in water) | 108.25 |
| Thickener (XB-23) | 4.00 |
| Ethanol | 8.00 |
| Water | 329.75 |
| Palm oil | 50.00 |
| | 500.00 grms. |

The foregoing formulation stimulated the flow of latex by an amount of 329% as compared with the control at 100%.

EXAMPLE C

Another formulation employing palm oil was composed of the following:

| | |
|---|---|
| Ethephon (same as in Example A) | 126.40 |
| Thickener (XB-23) | 4.00 |
| Ethanol | 8.00 |
| Water | 311.60 |
| Palm Oil | 50.00 |
| | 500.00 grms. |

The foregoing formulation stimulated the flow of latex by an amount of 331% over control (100%).

EXAMPLE D

In this example the proportion of Malaysian palm oil was raised by 50% as follows:

| | |
|---|---|
| Ethephon (same as in Example A) | 126.40 |
| Thickener (XB-23) | 3.75 |
| Ethanol | 7.50 |
| Water | 287.35 |
| Palm Oil | 75.00 |
| | 500.00 grms. |

This formulation stimulated the flow of latex by an amount of 390% over control (100%).

EXAMPLE E

For all remaining examples the thickener is XB-23.

In this example the Malaysian palm oil proportion was increased so as to double the amount present in Example C in the following formulation:

| | |
|---|---|
| Ethephon (see Example A) | 126.40 |
| Thickener | 3.33 |
| Ethanol | 6.67 |
| Water | 263.60 |
| Palm oil | 100.00 |
| | 500.00 grms. |

In this example the flow of latex was stimulated by 407% over control (100%).

EXAMPLE F

Instead of employing a thickener, the ethephon was formulated as a heavy invert emulsion. An anti-oxidant was included in the oil phase to prevent polymerization of the palm oil.

| | |
|---|---|
| Ethephon (same as in Example A) | 126.40 |
| Anti-Oxidant (butylated hydroxy anisole) | 3.25 |
| Emulsifier (Atlas G128 cationic nonionic blend) | 46.75 |
| Palm oil | 323.60 |
| | 500.00 grms. |

The foregoing invert emulsion formulation was prepared by adding the ethephon to an oil phase consisting of palm oil, anti-oxidant and emulsifying agent. A stable invert emulsion was formed having an external oil system and an internal aqueous system comprising ethephon, propylene glycol and water.

The invert emulsion formulation stimulated latex by an amount of 421% over control (100%).

EXAMPLE G

The following example shows the inclusion of a bactericide as well as an anti-oxidant. A latex stimulant was prepared having the following components:

| | |
|---|---|
| Ethephon (same as in Example A) | 2.185 |
| Biopolymer XB-23 | 0.069 |
| Ethanol, 3-A grade | 0.138 |
| Dowcil 100 (Bactericide) (1-(3 . chloroallyl) . 3,5,7 triaza, 1-Azania adamantane chloride) | 0.035 |
| Water | 5.115 |
| Anti-Oxidant (butylated hydroxy anisole) | 0.010 |
| Xylene | 0.010 |
| Palm Oil | 1.080 |
| | 8.642 lbs. |

The foregoing formulation had a specific gravity of 1.038 and 20° C. It was prepared by stirring at room temperature the ethephon, Dowcil 100 and water together until solution was achieved. A slurry of the biopolymer and the ethanol is then prepared and added to the previous solution under vigorous stirring for fifteen minutes. To the foregoing was added a solution of the anti-oxidant, the xylene and the palm oil under continued agitation for another ten minutes. The viscosity of the formulation at 25° C. was measured employing a Brookfield Viscometer Model RVT, employing a Number 4 spindle at 20 rpm. The viscosity was measured at 3270 centipoises.

EXAMPLE H

Another satisfactory formulation incorporating a bactericide as well as an anti-oxidant was prepared with the following components:

| | |
|---|---|
| Ethephon (same as in Example A) | 25.28 |
| Biopolymer (XB-23) | 1.60 |
| Ethanol (3-A grade) | 3.20 |
| Dowcil 100 | 0.40 |
| Water | 56.78 |
| Anti-Oxidant (butylated hydroxy anisole) | 0.12 |
| Xylene | 0.12 |
| Palm oil | 12.50 |
| | 100.00 % by wt. |

EXAMPLE I

A satisfactory formulation incorporating a bark penetrant was prepared with the following components:

| | |
|---|---|
| Ethephon (same as in Example A) | 25.32 |
| Biopolymer (XB-23) | 1.67 |
| Ethanol (3-A grade) | 3.33 |
| Dowcil 100 | 0.40 |
| Water | 46.78 |
| Dioctylphthalate (bark penetrant) | 10.00 |
| Palm oil | 12.50 |
| | 100.00 % by wt. |

EXAMPLE J

| | |
|---|---|
| Ethephon (same as in Example A) | 2.2084 |
| Biopolymer (XB-23) | 0.1395 |
| Ethanol (3-A grade) | 0.2791 |
| Dowcil 100 | 0.0296 |
| Dioctylphthalate (bark penetrant) | 1.5264 |
| Water | 4.5380 |
| | 8.7210 lbs. |

The foregoing formulation did not contain any palm oil and had a specific gravity of 1.048 at 20° C.

EXAMPLE K

Another useful latex stimulant had the following formulation:

| | |
|---|---|
| Ethephon (same as in Example A) | 2.2138 |
| Biopolymer (XB-23 | 0.1398 |
| Ethanol (3-A grade) | 0.2798 |
| Dowcil 100 | 0.0306 |
| Water | 6.0794 |
| | 8.7434 lbs. |

It can be seen that the foregoing formulation did not contain palm oil and that the Dowcil component is useful in preventing the gum thickener from degrading. This formulation had a specific gravity of 1.051 at 20° C. The viscosity of the formulation at 25° C. was measured employing a Brookfield Viscometer Model RVT, employing a number 4 spindle at 20 rpm. The viscosity was measured at 7470 centipoises.

EXAMPLE L

The following example incorporates a silicone oil as a water repellent agent to prevent washing away in heavy tropical rainstorms. This formulation contained the following:

| | |
|---|---|
| Ethephon (same as in Example A) | 25.32 |
| Biopolymer (XB-23) | 1.60 |
| Ethanol (3-A grade) | 3.20 |
| Dowcil 100 | 0.35 |
| Silicone oil water repellent | 2.50 |
| Water | 67.03 |
| | 100.00 % by wt. |

The formulation was made by preparing a mixture of the biopolymer and the ethanol that was added rapidly to a vessel containing the ethephon, Dowcil and water under agitation. After stirring for five minutes the silicone oil was added followed by additional stirring until a uniform mixture is achieved.

It can be seen that the various latex stimulants set forth hereinabove are of a rather thick consistency which can be varied to suit local conditions and problems. The dramatic results achieved through the composition of the present invention as well as through the practice of the method of the present invention easily justify the costs of the growth regulant. Furthermore, the growth regulant needs no special formulation, but can be simply shipped either as a concentrate or in a form ready to use.

Without further elaboration the foregoing will so fully illustrate my invention that others may, by applying current or future knowledge, readily adapt the same for use under various conditions of service.

What is claimed as the invention is:

1. A composition having significant shelf life under tropical conditions comprising an aqueous medium containing an effective amount of 2-chloroethylphosphonic acid, a polysaccharide gum produced by the fermentation of a carbohydrate by the bacterium Xanthomonas campestris, said gum being present in an amount of from about 0.5 to about 2.5% by weight of the total composition; and said composition having a viscosity of at least 1,000 cps.

2. The composition of claim 1, wherein the 2-chloroethylphosphonic acid is of a technical grade of about 90% solution by weight with a variance of no greater than 2%.

3. The composition of claim 1, wherein said composition includes a substantial amount of a fat.

4. The composition of claim 1, wherein the composition includes a substantial amount of an oil.

5. The composition of claim 4, wherein said oil is palm oil.

6. The composition of claim 4, wherein said composition includes an anti-oxidant to retard rancidity and polymerization of the oil.

7. The composition of claim 1, wherein said composition includes a bactericide.

8. A method of stimulating the flow of latex from a rubber plant comprising applying to said plant an effective amount of a latex flow stimulant composition having significant shelf life under tropical conditions comprising:
(a) an aqueous medium containing 2-chloroethylphosphonic acid;
(b) a polysaccharide gum produced by the fermentation of a carbohydrate by the bacterium Xanthomonas campestris;
said gum being present in an amount of from about 0.5% to about 2.5% by weight of the total composition; and
said composition having a viscosity of at least 1,000 cps.

9. The method of claim 8, wherein the 2-chloroethylphosphonic acid is of a technical grade of about 90% solution by weight with a variance of no greater than 2%.

10. The method of claim 8, wherein said composition includes a substantial amount of a fat.

11. The method of claim 8, wherein said composition includes a substantial amount of an oil.

12. The method of claim 11, wherein said oil is palm oil.

13. The method of claim 11, wherein said composition includes an anti-oxidant to retard rancidity and polymerization of the oil.

14. The method of claim 8, wherein said composition includes a bactericide.

* * * * *